FURYLMETHYLOXIME ETHERS

DESCRIPTION OF THE INVENTION

It has been found that compounds of the formula:

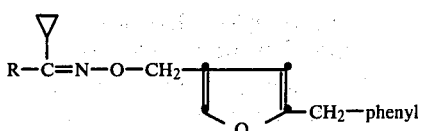
(I)

wherein R is naphthyl, phenyl, halophenyl, alkylphenyl or alkoxyphenyl, exhibit useful insecticidal activity.

In these compounds, each alkyl moiety preferably contains from one to four carbon atoms, and suitably is of either straight-chain or branched-chain configuration. By "halogen" is meant fluorine, chlorine and bromine. When substituted, it is preferred that the phenyl moiety is substituted at the para-position of the ring.

The compounds of Formula I exhibit geometric isomerism about the oximic double bond, and the present invention includes the individual E- and Z-isomers and mixtures thereof.

The compounds of Formula I can be prepared by reacting an alkali metal salt of a ketoxime of the general formula

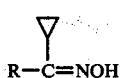
(II)

wherein R has the meaning given for Formula I, with a compound of the general formula

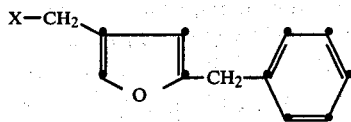
(III)

wherein X represents a chlorine, bromine or iodine atom, preferably a chlorine or a bromine atom, especially a chlorine atom.

The reaction is preferably carried out in the presence of a polar aprotic solvent. Particularly suitable solvents are anhydrous acetonitrile, dimethylformamide in toluene, or tetrahydrofuran. Reaction temperatures in the range 60°–150° C., preferably in the range 90°–110° C., and reaction times of 2 to 10 hours, may be used. Alternatively, the reaction may be carried out in a two-phase organic/inorganic system in the presence of a phase transfer catalyst. The phase transfer catalyst may be any reagent which will accelerate interphase reactions in organic/inorganic two-phase systems. The alkali metal salt of the ketoxime of formula II may be prepared by the reaction of an alkali metal hydride, for example sodium hydride, with the ketoxime, or by reaction of aqueous potassium or sodium hydroxide with the ketoxime. The alkali metal salt of the ketoxime is preferably prepared in situ.

The compounds of the general Formula III may be prepared by the reaction of 2-benzyl-4-hydroxymethylfuran with a suitable halogenating agent, for example thionyl chloride, suitably in an inert solvent in the presence of a base, for example pyridine.

The compounds of the invention have exhibited pesticidal, especially insecticidal, activity. The invention therefore provides a pesticidal composition which comprises as active ingredient a compound of the general Formula I, together with a suitable carrier. The invention also provides a method of combating pests at a locus, which comprises applying to that locus a compound of the general Formula I or a pesticidal composition according to the invention. The invention further provides the use of a compound of the general Formula I as a pesticide.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be formulated as wettable powders, dusts, granules, solutions, emulsifi-

COMBATING FUNGI WITH 1-(ω-SUBSTITUTED PENTYL)-3-(2-CYANO-ACETYL)-UREAS

The present invention relates to and has for its objects the provision of particular new 1-(ω-substituted pentyl)-3-(2-cyano-acetyl)-ureas which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

As has already been known for a long time, zinc ethylene-1,2-bis-dithiocarbamidate and N-trichloromethylthio-tetrahydrophthalimide may be used as fungicides in agriculture and in horticulture; amongst the commercial products, the compounds mentioned are of great importance (see R. Wegler, "Chemie der Pflanzenschutz- and Schadlingsbekampfungsmittel" ("Chemistry of Plant Protection Agents and Agents for Combating Pests"), Volume 2, pages 65 and 108, Berlin/Heidelberg/New York (1970)). However, the action is not always satisfactory when low concentrations are used. In addition, these fungicides cannot be used curatively.

Furthermore, the fungicidal action of some isonitrosocyanoacetamide derivatives is known (in this context see DT-OSS (German Published Specifications) Nos. 1,693,052, 2,118,317, 2,312,956, 2,350,910, 2,436,654, 2,436,655, 2,603,643 and 2,635,967 and U.S. Pat. Nos. 3,625,987, 3,769,423, 3,919,284, 3,954,992 and 3,957,847). In this case also the activity cannot be relied upon when low amounts are used and damage to plants is observed at normal concentrations.

The present invention now provides, as new compounds, the ω-substituted pentyl-urea derivatives of the general formula

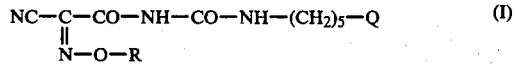

in which
R represents $R^1$, $CO-R^2$, $CO-NH-R^3$ or $CO-OR^4$, wherein
$R^1$ represents unsubstituted alkyl with 1 to 10 carbon atoms; or represents substituted alkyl with 1 to 4 carbon atoms, which contains as a substituent, a vinyl group, an alkynyl group with up to 4 carbon atoms, an alkylcarbonyl group with 2 to 5 carbon atoms, an alkoxycarbonyl group with 2 to 5 carbon atoms, an alkenoxycarbonyl or alkynoxycarbonyl group with 4 to 5 carbon atoms, an aminocarbonyl group, an N-alkylaminocarbonyl or N-cycloalkylaminocarbonyl group with up to 7 carbon atoms in either case or a N-phenylaminocarbonyl group, which can optionally have $C_1-C_4$ alkyl and/or chlorine as further substituents on the phenyl radical; or represents benzyl, which can be substituted in the aromatic part by a methyl, methoxy, methylenedioxy, nitro, trifluoromethyl, benzoyl, monochlorobenzoyl or dichlorobenzoyl, phenyl or phenoxy group or by 1 to 4 chlorine atoms;
$R^2$ represents a straight-chain or branched, saturated or unsaturated hydrocarbon radical with up to 8 carbon atoms, which can be substituted by chlorine or bromine or by a cyano group,
$R^3$ represents a straight-chain or branched alkyl radical with up to 11 carbon atoms, which can be substituted by a cyano group or by an alkoxycarbonyl radical with up to 5 carbon atoms, or represents a methyl, nitro or trifluoromethyl group or by chlorine,
$R^4$ represents a saturated or unsaturated aliphatic group with up to 4 carbon atoms and
Q represents CN, $CO-NH_2$, COOH or $CO-OR^5$, wherein
$R^5$ denotes an alkyl group with 1 to 4 carbon atoms.
The compounds of the formula (I) have powerful fungicidal properties.

Preferably, R represents $R^1$. Preferably, $R^1$ represents alkyl with 1 to 6 carbon atoms; or represents alkyl with 1 or 2 carbon atoms, which is substituted by a vinyl group, by an alkylcarbonyl group with 2 to 5 carbon atoms, by alkoxycarbonyl with 2 to 5 carbon atoms, by aminocarbonyl, by N-alkylaminocarbonyl or N-cycloalkylaminocarbonyl each with up to 7 carbon atoms, or by N-phenylaminocarbonyl, which can contain $C_1-C_4$ alkyl and/or chlorine as substituents on the phenyl radical; or represents benzyl, which can carry a methyl, methoxy, methylenedioxy, nitro or trifluoromethyl group or 1 or 2 chlorine atoms as substituents in the aromatic part.

R particularly preferably represents methyl, ethyl, methoxycarbonylmethyl, 1-(methoxycarbonyl)-ethyl, tert.butylcarbonylmethyl or aminocarbonylmethyl.

An interesting active compound is that compound of the general formula (I) in which R represents methyl and Q represents CN.

As oxime derivatives, the substances according to the invention can have two different geometric structures:

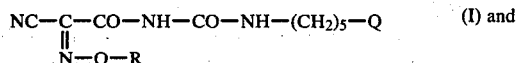

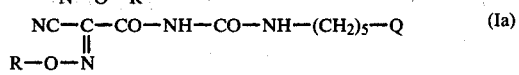

The indication of the steric structure is dispensed with herein; for the purposes of the present specification, the indicated formula (I) and analogous formulae are intended, in each case, also to include the corresponding structure according to the formula (Ia).

The compounds according to the invention exhibit a very good fungicidal action. They can be used protectively, curatively and even eradicatively, and in addition they have systemic and/or locosystemic properties. Surprisingly, they are better tolerated by plants than the isonitrosocyano acetamide derivatives which are known from the state of the art. Compared with the dithiocarbamidates and N-trichloromethylthio-tetrahydrophthalimide, they have the advantage of curative and eradicative action.

The compounds according to the invention already represent a valuable enrichment of the art because of the many possibilities of their superior biological application. Furthermore, new active compounds having properties which are valuable in practice are made available at a time when there is a marked demand for new fungicides because of resistance phenomena towards previous active compounds.

No. 1,913,273), ω-phenoxycarbonylamino-caproic acid (DT-OS (German Published Specification) No. 1,720,606 and Chem. Abstr. 71,50689, (1969) or ω-isocyanato-caproic acid chloride (DT-AS (German Published Specification) No. 1,222,919), dissolved or suspended in an inert solvent, for example toluene, with ammonia. If ω-phenoxycarbonylamino-caproic acid is employed as the starting material, 5-carboxypentyl-urea is obtained as the ammonium salt. The free ureidopentylcarboxylic acid is formed by acidifying with a mineral acid. The ω-substituted 1-pentyl-urea is now reacted with excess cyanoacetic acid in the presence of a carboxylic acid anhydride to give the 1-(5-substituted pentyl)-3-(2-cyanoacetyl)-urea; toluene can be used as the solvent. In a third stage, the said urea is brought to a pH value of about 4 to 6, preferably to a pH value of about 5 to 5.6, in water or a mixture of water with methanol, ethanol, propanol, glycol monomethyl ether, glycol monoethyl ether, acetonitrile, dioxane or tetrahydrofuran, with a salt of nitrous acid at a temperature from about 20° to 70° C., preferably about 40° to 50° C., by adding an organic carboxylic acid, for example acetic acid, or a mineral acid, for example sulphuric acid, or also by means of a mixture of an organic carboxylic acid with a mineral acid. After about 2 hours, the oximation reaction has ended. The reaction mixture is adjusted to a pH value of about 1.8 to 3.5, preferably of about 2, by adding further mineral acid at a temperature which is between the freezing point of the solution and about 30° C., preferably about 2° to 10° C. The 1-(5-substituted pentyl)-3-(2-cyano-2-hydroximino-acetyl)-urea of the formula (IV) is either separated out by diluting the reaction mixture with water and washed with water, after separating off the product, and dried, or the compound is taken up in a solvent, such as ethyl acetate, methyl acetate, ethyl formate or methyl propionate, the resulting solution of the reaction product is extracted by washing with water, the reaction mixture is dried with, for example, sodium sulphate and the product (IV) is precipitated by adding petroleum ether, or the solution is evaporated.

Finally, the urea of the formula (IV) can also be obtained by the action of an ester of nitrous acid, for example isoamyl nitrite, on a 1-(5-substituted pentyl)-3-(2-cyanoacetyl)-urea.

Alkylating agents of the formula (V) required for process variant (b) are known compounds which are customary in the laboratory. They can be obtained by processes which are known in principle. Examples of starting materials of the formula (V) are: dimethyl sulphate, diethyl sulphate, 2-bromobutane, 1-iodopentane, 1-bromohexane, 1-bromodecane, allyl chloride, methallyl chloride, 1-chlorobut-2-ene, propargyl chloride, 1-chloroacetone, 1-bromo-3,3-dimethyl-butan-2-one, 2-bromo-4,4-dimethyl-pentane-3-one, bromoacetic acid methyl ester, chloroacetic acid sec.-butyl ester, 2-bromovaleric acid butyl ester, 4-chlorobutyric acid ethyl ester, chloroacetamide, N-methylchloroacetamide, N-ethyl-chloroacetamide, N-sec.-butyl-chloroacetamide, N-hexylchloroacetamide, N-cyclopropylchloroacetamide, N-cyclopentylchloroacetamide, N-cyclohexylchloroacetamide, bromoacetanilide, N-2-ethylphenyl-, N-2-methylphenyl-, N-2-isopropylphenyl-, N-2-tert.-butylphenyl-, N-3-methylphenyl-, N-4-methylphenyl-, N-2,6-dimethylphenyl-, N-2-chlorophenyl-, N-3-chlorophenyl-, N-4-chlorophenyl-, N-3,4-dichlorophenyl-, N-3,5-dichlorophenyl- and N-2-methyl-4-chlorophenyl-chloroacetamide, -2-chloropropionamide and -2-chlorobutyramide, benzyl chloride, 2-, 3- or 4-xylyl chloride, 2-, 3- or 4-methoxybenzyl bromide, 3,4-methylenedioxybenzyl chloride, 3-nitrobenzyl chloride, 4-nitrobenzyl chloride, 4-trifluoromethylbenzyl chloride, 2-, 3- or 4-chlorobenzyl chloride, 3,4-dichlorobenzyl chloride, 2-phenylbenzyl chloride, 4-phenyl-benzyl chloride, 4-benzoyl-benzyl chloride, 4-(2-, 3- or 4-chlorobenzoyl)-benzyl chloride, 4-(2,3-, 2,4-, 2,5-, 2,6-, 3,4- or 3,5-dichlorobenzoyl)-benzyl chloride, 2-, 3- or 4-phenoxybenzyl chloride and ar.-tetrachloro-o-, tetrachloro-m- and tetrachloro-p-xylyl chloride.

The acid anhydrides and acid halides of the formula (VI) required for process variant (c) are compounds which are customary in the laboratory. There may be mentioned here: acetic anhydride, propionic anhydride, chloroacetyl chloride, dichloroacetyl chloride, trichloroacetyl chloride, 2,3-dibromopropionyl chloride, isobutyryl chloride, 2-chloroisobutyryl chloride, valeryl chloride, isovaleryl chloride, 2-ethylhexanoyl chloride, cyanoacetyl chloride, acryloyl chloride, methacryloyl chloride and crotonoyl chloride.

The isocyanates of the formula (VII) and the carbamoyl halides of the formula (VIII) required for process variant (d) are also known compounds; the carbamoyl halides are prepared by the addition of hydrogen halide onto the isocyanates of the formula (VII).

The following compounds may be mentioned here: methyl, ethyl, propyl, butyl, isobutyl, hexyl and decyl isocyanate or methyl-, ethyl-, propyl-, butyl-, isobutyl-, hexyl- and decylcarbamoyl chloride, ω-cyanoethyl isocyanate, 1-cyano-1-methylethyl isocyanate, ω-cyanopropyl isocyanate, ω-cyanopentyl isocyanate, ω-cyanohexyl isocyanate, ω-cyanooctyl isocyanate, ω-cyanononyl isocyanate, ω-cyanodecyl isocyanate, ω-cyanoundecyl isocyanate, methoxycarbonylmethyl isocyanate, ethoxycarbonylmethyl isocyanate, butoxycarbonylethyl isocyanate, isobutoxycarbonylethyl isocyanate, 1-methoxycarbonyl-1-methyl-ethyl isocyanate, 1-propoxycarbonyl-1-methyl-ethyl isocyanate, 1-ethoxycarbonyl-1-ethyl-ethyl isocyanate, 1-isobutoxycarbonyl-1-ethyl-ethyl isocyanate, methoxycarbonyl-propyl isocyanate, methoxycarbonyl-pentyl isocyanate, isopropoxycarbonylpentyl isocyanate, sec.-butoxycarbonyl-pentyl isocyanate, 2-ethoxycarbonyl-2-ethyl-butyl isocyanate, γ-ethoxycarbonyloctyl isocyanate, methoxycarbonyl-decyl isocyanate, ethoxycarbonyl-decyl isocyanate, propoxycarbonyl-decyl isocyanate, butoxycarbonyl-decyl isocyanate, methoxycarbonylundecyl isocyanate, phenyl isocyanate, 2- and 4-tolyl isocyanate, 3- and 4-nitrophenyl isocyanate, 2-, 3- and 4-chlorophenyl isocyanate, 3,4-dichlorophenyl isocyanate, 3,5-dichlorophenyl isocyanate and 2-trifluoromethyl isocyanate.

The carbonic acid esters (IX) required in process variant (e) are also known compounds. There may be mentioned: dimethyl pyrocarbonate, diethyl pyrocarbonate, chloroformic acid ethyl ester, chloroformic acid methyl ester, chloroformic acid isopropyl ester, chloroformic acid sec.-butyl ester, chloroformic acid isobutyl ester, chloroformic acid allyl ester and chloroformic acid methallyl ester.

For the preparation of the compounds according to the invention by process variant (a), the 2-cyano-2-alkoximinoacetamide is converted into the anion of the amide in an inert anhydrous solvent, such as dioxane, tetrahydrofuran or diisopropyl ether, using, for example, sodium hydride or potassium tert.-butylate, and the product is then reacted with the ω-substituted pentyl isocyanate at moderately elevated temperature. After the reaction has ended, the mixture is weakly acidified in the cold with an organic carboxylic acid and thereafter the reaction product according to the invention is precipitated by adding water, or the solution of the reaction product in the organic solvent is extracted by washing and carefully evaporated.

For the preparation of those compounds of the formula (I) in which R represents $R^1$ by process variant (b), the reaction is preferably carried out in the presence of a polar solvent, such as dimethylsulphoxide, dimethylformamide, dimethylacetamide, acetone, methyl ethyl ketone, methylene chloride, chloroform, chlorobenzene, toluene, dioxane, tetrahydrofuran, acetonitrile, benzonitrile or ethyl acetate.

Acid-binding agents which can be used in process variant (b) are all the customary hydrogen halide acceptors. These include alkali metal hydroxides, alkali metal carbonates and other suitable alkali metal salts. Examples which may be mentioned are sodium carbonate, sodium bicarbonate, borax (disodium tetraborate) and trilithium phosphate. If the reaction is carried out in the presence of water, the mixture can be neutralized by adding sodium hydroxide solution. Furthermore, it is possible to use organic acid-binding agents, for example tertiary amines. There may be mentioned here triethylamine, dimethylbenzylamine, dimethylaniline, pyridine, picoline, quinoline, ethyl diisopropylamine and ethyl dicyclohexylamine.

In process variant (b), the reaction temperatures can be varied within a relatively wide range. In general, the reaction is carried out at about $-50°$ to $+120°$ C., preferably about $-5°$ to $+80°$ C.

The reactions can also be carried out in a mixture of water and a water-miscible organic solvent, or in a heterogeneous system consisting of water and a solvent which is not water-miscible or only partly water-miscible; in this case, the temperature range of the reaction is between the freezing point of water or the solidifying point of the aqueous solution and 100° C., preferably at about $-5°$ to $+80°$ C.

However, if the salts of the urea of the formula (IV) are used as starting materials in process variant (b), the reaction must be carried out at low temperatures, preferably at about $-30°$ C. to $-10°$ C., and the mixture must be weakly acidified after the reaction has ended.

The reaction temperatures and reaction time in process (b) are determined by the activity of the starting materials of the formula (V). A small amount of an iodide is appropriately added to the mixtures before the reaction if a compound of the formula (V) containing iodine as the leaving group is not directly employed. By means of this addition, the rate of reaction is increased and the danger of the formation of compounds having a nitrone structure is reduced (in this context see Houben-Weyl, "Methoden der organischen Chemie", ("Methods of Organic Chemistry"), Volume 10/4, Stuttgart (1968)).

The comments given for process variant (b) also apply, with due alteration of the details, to process variant (f), when a carboxylic acid of the formula (X) is to be reacted to give a product of the formula (I) in which R represents $R^1$ and Q represents the group $CO-OR^5$.

The preparation of the compounds of the formula (I) in which R represents $CO-R^2$ by process variant (c) is carried out in an anhydrous organic solvent at a temperature of about $-50°$ C. to $+120°$ C., preferably at about 0° to 50° C., a tertiary amine being employed to bind the acid.

Process variant (d) is appropriately carried out in a diluent. Possible diluents are all the inert organic solvents, especially dimethylsulphoxide, dimethylformamide, dimethylacetamide or ethyl acetate; ketones, for example acetone, methyl ethyl ketone and diethyl ketone; ethers, for example tetrahydrofuran; chlorinated hydrocarbons, for example methylene chloride and chloroform; nitriles, for example acetonitrile and benzonitrile; and aromatic compounds, for example toluene and chlorobenzene.

It is possible to use, as auxiliaries, basic catalysts in process variant (d), for example tertiary amines, such as triethylamine or pyridine, or tin 2-ethyl-hexanoate. Instead of the isocyanate of the formula (VII), it is possible to use in each case the corresponding carbamoyl halide of the formula (VIII). In this case, additional tertiary amine is necessary to bind the hydrogen halide acid liberated during the reaction.

The reaction temperatures in process variant (d) can be varied within a relatively wide range. In general, the reaction is carried out at about $-20°$ and $+120°$ C., preferably about $+10°$ to 70° C.

The preparation of the compounds of the formula (I) in which R represents $CO-O-R^4$ by process variant (e) is carried out analogously to the procedure used in process variant (b).

Depending on the reaction conditions, the active compounds according to the invention are precipitated in the crystalline form or they remain dissolved in the organic solvent and can then be separated out after extracting the solution by washing with water, by carefully concentrating the solution or by adding a slightly polar, organic solvent, such as carbon tetrachloride, cyclohexane or dibutyl ether.

If the compounds according to the invention are dissolved in a water-miscible solvent, they can also be precipitated out by adding water. To the extent that the particular conditions of the working up processes allow, the solutions of the active compounds according to the invention or the suspensions of the active compounds which are still moist from solvent should be rendered weakly acid.

Some of the compounds according to the invention decompose at a relatively high temperature; in these cases, the melting points can be determined only with low accuracy or not at all. The presence of certain structural elements can be seen from the NMR spectra. The IR spectra also exhibit characteristic absorption bands.

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention can be used against parasitic fungi which infect above-ground parts of plants or attack the plants through the soil, as well as against seed-borne pathogens. Accordingly, they can also be used for the treatment of soil and for the treatment of seed.

The active compounds in particular exhibit a high protective and curative activity against Phycomycetes.

In addition, good effects against species of Mycosphaerella and species of Rhizoctonia and against rust fungi can be observed.

The active compounds according to the invention not only exhibit the good properties of outstanding commercially available formulations, but in addition possess considerable advantages. These reside, in the first place, in the ability of the compounds according to the invention to penetrate into the plant. The compounds can be taken up by the surface of the seed, by the roots and also by the above-ground plant organs after external application. Furthermore, the compounds possess the advantageous ability of exerting a loco-systemic effect, that is to say to exert a depth effect in the plant tissue and in doing so to eliminate fungal pathogens which have already penetrated into the tissue of the host plant.

Within a certain concentration range, some of the compounds according to the invention are also active as growth regulators for plants.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

In addition to the above possible formulations, it should be noted that the compounds according to the invention can be formulated together with sucrose, dextrose, dextrins, anhydrous calcium sulphate or calcium sulphate hemihydrate, as well as with carboxylic acids, for example fumaric acid or 4-hydroxybenzoic acid, and also with weakly acid ion exchangers.

The active compounds according to the invention can be present in the formulations as a mixture with other active compounds, such as fungicides, insecticides, acaricides, nematicides, herbicides, bird repellants, growth factors, plant nutrients and agents for improving soil structure.

The formulations in general contain from 0.1 to 95 percent by weight of active compound, preferably from 0.5 to 90 percent.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomizing, dusting, scattering, dry dressing, moist dressing, wet dressing, slurry dressing or encrusting.

Especially when used as leaf fungicides, the active compound concentrations in the use forms can be varied within a fairly wide range. They are, in general, from 0.5 to 0.0005 percent by weight, preferably from 0.2 to 0.001 percent.

In the case of the treatment of seed, amounts of active compound of 0.01 to 50 g, preferably 0.5 to 5 g, are generally employed per kilogram of seed.

For the treatment of soil, amounts of active compound of 1 to 1,000 g, preferably of 10 to 200 g, are generally employed per cubic meter of soil.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is illustrated in the following examples:

EXAMPLE 1

(a) Precursor

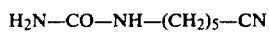

1.019 g of ω-cyanopentyl isocyanate were dissolved in 4.8 liters of dry toluene. Ammonia was passed over the solution, while stirring, until no more was absorbed. The reaction product separated out. It was separated off, washed with toluene, isopropanol and with water and dried at 60° C. and under a pressure of 0.1 mm Hg. Yield: 1.092 g of 1-(5-cyanopentyl)-urea. Melting point 143°–144° C.

The compound could also be prepared from 5-aminocaproic acid nitrile and potassium cyanate.

(b) Intermediate

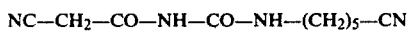

135.6 g (1.32 mols) of acetic anhydride were added to 90.4 g (1.06 mols) of cyanoacetic acid, 163 g (1.05 mol) of 1-(5-cyanopentyl)-urea and 200 ml of dry toluene in the course of 35 minutes. The reaction mixture was warmed to 60° to 67° C. for 3 hours. The reaction solution was filtered at about 70° C. On cooling, the reaction product separated out. It was filtered off, washed with toluene and dried at 60° C. and under a pressure of 0.1 mm Hg. Yield: 137.8 g of 1-(5-cyanopentyl)-3-(2-cyanoacetyl)-urea. Melting point 112° C. The compound could be recrystallized from toluene, ethyl acetate or from water. Melting point 113.5° C.

(c) Starting material

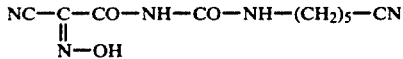

550 g (2.47 mols) of 1-(5-cyanopentyl)-3-(2-cyanoacetyl)-urea, 625 g of water; 625 g of dioxane and 188 g of technical grade sodium nitrite were adjusted to a pH value of 5 at 50° C. by slowly adding about 15% strength sulphuric acid. The mixture was stirred for two hours and 5 liters of water and 5 liters of ethyl acetate were then added. The mixture was cooled to 2° C. and the pH value was adjusted to 2 by further addition of 15% strength sulphuric acid. The organic phase was separated off and the aqueous phase was stirred a second time with 2 liters of ethyl acetate. The ethyl acetate solution was washed twice with 2 liters of water, which contained a small amount of sodium sulphate for better separation, each time and dried twice over sodium sulphate. The reaction product was precipitated by adding petroleum ether. The product was washed with a mixture of petroleum ether and ethyl acetate in the ratio 4:1 and dried at 60° C. and under a pressure of 0.1 mm Hg. Yield: 504 g of 1-(5-cyanopentyl)-3-(2-cyano-2-hydroximino-acetyl)-urea of melting point 147° C.

A further second crystalline fraction could be obtained from the mother liquor by concentration (about 70 g).

The product could be recrystallized from water, diethyl ketone or ethyl acetate for further purification.

(d)

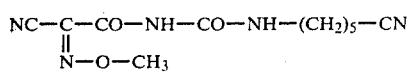

The preparation was carried out according to process variant (b).

500 g of 1-(5-cyanopentyl)-3-(2-cyano-2-hydroximinoacetyl)-urea (1.99 mols) 2 liters of acetonitrile and 260 g of dimethyl sulphate (2.06 mols) were initially introduced at 40° C. An amount of a solution of 84 g of sodium hydroxide dissolved in 440 ml of water was added in the course of about 22 minutes, while stirring thoroughly, so that the pH value reached about 8. The reaction mixture was then immediately adjusted to a pH value of 5. The reaction product was precipitated by adding ice. It was separated off, washed with water until salt-free and dried at 60° C. and under a pressure of 1 mm Hg. Yield: 503 g of 1-(5-cyanopentyl)-3-(2-cyano-2-methoxyimino-acetyl)-urea of melting point 92° C., that is to say 95% of theory. The compound could be recrystallized from water or isopropyl alcohol.

EXAMPLE 2

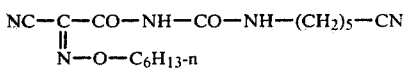

The preparation was carried out according to process variant (b).

25.1 g (0.1 mol) of 1-(5-cyanopentyl)-3-(2-cyano-2-hydroximino-acetyl)-urea, 100 ml of acetonitrile and 17 g of 1-bromohexane were initially introduced at 40° C. and 13 g of ethyl diisopropylamine were added dropwise in the course of 30 minutes. The mixture was kept at 40° C. for a further 30 minutes and 1 ml of acetic acid, 400 ml of methylene chloride and water were added. The methylene chloride solution was extracted by washing three times with water and evaporated in vacuo. After treatment with petroleum ether, the residue crystallized. Yield: 25 g of 1-(5-cyanopentyl)-3-(2-cyano-2-hexyloximinoacetyl)-urea. Melting point 47° C.

EXAMPLE 3

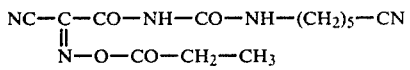

The preparation was carried out according to process variant (c).

25.1 g (0.1 mol) of 1-(5-cyanopentyl)-3-(2-cyano-2-hydroximino-acetyl)-urea, 100 ml of acetonitrile and 9.3 g (0.1 mol) of propionyl chloride were initially introduced and 7.9 g of pyridine were added dropwise. After 18 hours, the reaction mixture was filtered and the compound according to the invention was precipitated by adding ice, separated off, washed with water and dried at 60° C. and under a pressure of 0.1 mm Hg. Yield: 26.6 g of 1-(5-cyanopentyl)-3-(2-cyano-2-propionyloximino-acetyl)-urea. Melting point 116.5° C.

could be prepared by methods analogous to those described in the above examples:

TABLE 1

| Compound No. | Preparation according to process variant | R | Melting point (°C.) |
|---|---|---|---|
| 5 | b | $C_2H_5$ | 105.5 |
| 6 | b | $CH(CH_3)-CO-O-CH_3$ | 126.5 |
| 7 | b | $CH_2-CO-O-CH_3$ | 115.5 |
| 8 | b | $CH_2-CO-C(CH_3)_3$ | 134 |
| 9 | b | $CH_2-CO-NH_2$ | 160 |
| 10 | b | $CH_2-CO-NH-$(2-ethylphenyl) | 157.5 |
| 11 | b | $CH_2-$phenyl | 96 |
| 12 | b | $CH_2-$biphenyl | 138 |
| 13 | b | $CH_2-$(3,4-methylenedioxyphenyl) | 105 |
| 14 | c | $CO-C(CH_3)_3$ | 115 |
| 15 | c | $CO-CH_2Cl$ | 113 |
| 16 | c | $CO-O-CH_3$ | 130 |
| 17 | c | $CO-O-CH(CH_3)_2$ | 139 |
| 18 | d | $CO-NH-(CH_2)_5-CN$ | 97; IR (KBr): CO 1795 cm$^{-1}$ |
| 19 | d | $CO-NH-$phenyl | 138.5–146 (decomposition); IR (KBr): CO 1,800–1,805 cm$^{-1}$ |
| 20 | b | $CH_2-CH=CH_2$ | 88 |
| 21 | b | $CH_2-C\equiv CH$ | 126 |

EXAMPLE 4

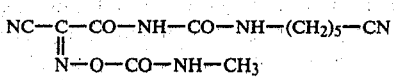

$$NC-\underset{\underset{N-O-CO-NH-CH_3}{\|}}{C}-CO-NH-CO-NH-(CH_2)_5-CN \quad (4)$$

The preparation was carried out according to process variant (d).

25.1 g (0.1 mol) of 1-(5-cyanopentyl)-3-(2-cyano-2-hydroximino-acetyl)-urea, 100 ml of dry acetonitrile and 6 g of methyl isocyanate were initially introduced. 100 mg of triethylenediamine were added. 1-(5-Cyanopentyl)-3-(2-cyano-2-methylaminocarbonyl-oximino-acetyl)-urea was formed in the exothermic reaction. It was filtered off, washed with acetonitrile and dried at 60° C. and under a pressure of 0.1 mm Hg. Melting point 141.5°–146.5° C. (decomposition) IR (CHCl$_3$): CO 1,805 cm$^{-1}$.

The following compounds of the general formula

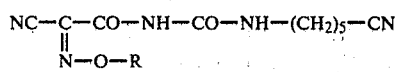

$$NC-\underset{\underset{N-O-R}{\|}}{C}-CO-NH-CO-NH-(CH_2)_5-CN \quad (Ib)$$

EXAMPLE 5

(a) Precursor $$H_2N-CO-NH-(CH_2)_5-CO-NH_2$$

502 g (2 mols) of phenoxycarbonylamino-caproic acid, 1.2 liters of chlorobenzene, 0.6 liters of ethylene chloride, 0.4 g of antimony trichloride and 1 g of dimethylformamide were initially introduced, while cooling externally with ice. 256 g (2.15 mol) of thionyl chloride were added dropwise at 9° C. in the course of 90 minutes. The reaction mixture was stirred for a further 4 hours. Some of the solvent was then distilled off up to a sump temperature of 31° C. under 11 mm Hg. Ammonia was then passed over the reaction mixture at −20° C. until no more was absorbed. After adding 1.6 liters of 31% strength aqueous ammonia solution, the mixture was slowly heated to the boil and kept at the boiling point for about 8 hours. The crystals were separated off, washed with water and dried at 70° C. in vacuo. Yield 171 g of 1-(5-aminocarbonyl-pentyl)-urea of melting point 208° C.

(b) Intermediate

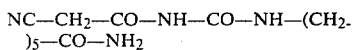

This intermediate was prepared analogously to the intermediate described in Example 1(b), starting from 1-(5-aminocarbonylpentyl)-urea. Melting point 164° C.

(c) Starting material

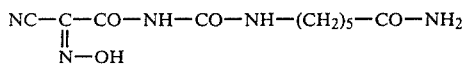

A mixture of 72 g of 1-(5-aminocarbonyl-pentyl)-3-(2-cyanoacetyl)-urea, 125 ml of water, 125 ml of dioxane, 23.2 g of sodium nitrite and 1 ml of acetic acid was adjusted to pH 4.5 to 5 at 50° C. by slowly adding 15% strength sulphuric acid dropwise. The reaction mixture was stirred at 50° C. for 2 hours, diluted with 600 ml of water and 600 ml of ethyl acetate, then cooled at 20° C. and adjusted to a pH value of 2. The crystals were separated off, washed with water and dried in vacuo. 61.3 g of 1-(5-aminocarbonyl-pentyl)-3-(2-cyano-2-oximinoacetyl)-urea of melting point 187°–189° C. were obtained.

(d)

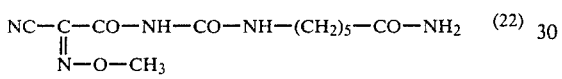 (22)

The compound was prepared according to process variant (b) by methylating the hydroxy compound of (c). Melting point 155° C.

EXAMPLE 6

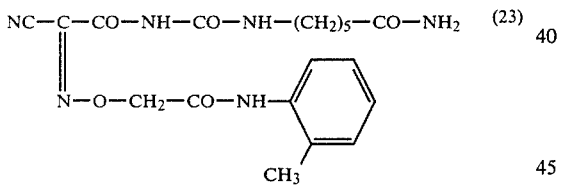 (23)

The compound was prepared according to the process variant (b). Melting point 172° C.

EXAMPLE 7

(a) Precursor

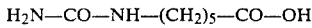

260.5 g (1.04 mol) of phenoxycarbonylamino-caproic acid were suspended in 500 ml of dioxane. 800 ml of 33% strength aqueous ammonia solution were added dropwise, while cooling externally. The mixture was brought to 90° C. in the course of 3 hours and kept at this temperature for 6 hours. Some of the solvent was distilled off, and the mixture was acidified to a pH value of 3 with sulphuric acid. After cooling the mixture to 3° C., the crystals were filtered off and washed with water. The yield was 116 g of 1-(5-carboxypentyl)-urea of melting point 167°–181° C.

(b) Intermediate

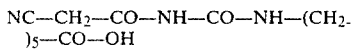

The intermediate was prepared according to the instructions given for the intermediate described in Example 1(b), starting from 1-(5-carboxypentyl)-urea. Melting point 158° C.

(c) Starting material

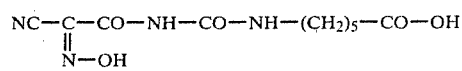

48.2 g (0.2 mol) of 1-(5-carboxypentyl)-3-(2-cyanoacetyl)-urea, 50 ml of water, 50 ml of dioxane and 15.2 g of sodium nitrite were warmed to 50° C. A mixture of 13 g of sulphuric acid and 90 g of water was then added dropwise in an amount such that a pH value of 4.6 resulted. The mixture was kept at 50° C. for a further 2 hours and then cooled to about 1° C., 400 ml of water were added and the pH value was lowered to 2.5 by adding further dilute sulphuric acid dropwise. The crystals were separated off, washed with water and dried at 60° C. in vacuo. The yield was 51.7 g of 1-(5-carboxypentyl)-3-(2cyano-2-hydroximinoacetyl)-urea of melting point 201° C.

(d)

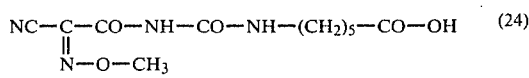 (24)

The preparation was carried out according to process variant (b). Melting point 167° C.

EXAMPLE 8

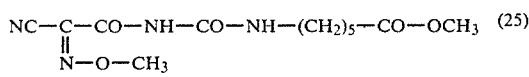 (25)

9.8 g of the compound according to Example 7, 100 ml of acetonitrile, 1.8 g of sodium carbonate and 4.8 g of dimethylsulphate were kept at 70° C. for 5 hours. The mixture was then cooled to 2° C., 100 g of water and ice were added and the crystals which had precipitated were separated off. These were washed with water to give 9 g of 1-(5-methoxycarbonylpentyl)-3-(2-cyano-2-methoxyiminoacetyl)-urea of melting point 91° C.

The fungicidal activity of the compounds of this invention is illustrated by the following examples wherein the compounds according to the present invention are each identified by the number (given in brackets) from the preparative examples hereinabove.

The known comparison compounds are identified as follows:

(A) = 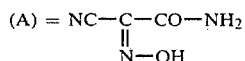

(B) = 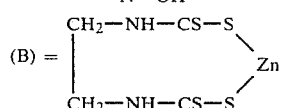

(C) = 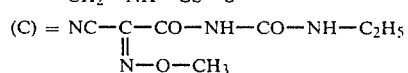

EXAMPLE 9

Phytophthora test (tomato)/protective

Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were sprayed with the spray liquid until dripping wet. The plants remained in a greenhouse for 24 hours at 20° C. and at a relative atmospheric humidity of 70%. The tomato plants were then inoculated with an aqueous spore suspension of *Phytophthora infestans*. The plants were brought into a moist chamber with an atmospheric humidity of 100% and a temperature of 18°–20° C.

After 5 days the infection of the tomato plants was determined. The assessment data were converted to percent infection: 0% meant no infection; 100% meant that the plants were totally infected.

The active compounds, the concentrations of the active compound and the results can be seen from the following table:

Table 2

| Phytophthora test (tomato)/protective | |
|---|---|
| Active compound | Infection in % at an active compound concentration of 0.001% |
| (A) | 17 |
| (1) | 1 |
| (5) | 9 |
| (2) | 15 |

EXAMPLE 10

Phytophthora test (tomato)/curative

Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated amount of emulsifier.

Young tomato plants with 2 to 4 foliage leaves were inoculated with an aqueous spore suspension of *Phytophthora infestans*. The plants remained for 7 hours at 20° C. and a relative atmospheric humidity of 100%.

After a short drying-off time, the plants were sprayed with the spray liquid, prepared in the manner described above, until dripping wet, and were then brought into a moist chamber at 100% atmospheric humidity and 18° to 20° C.

After 5 days the infection of the tomato plants was determined. The assessment data were converted to percent infection: 0% meant no infection: 100% meant that the plants were totally infected.

The active compounds, the concentrations of the active compound and the results can be seen from the following table:

Table 3

| Phytophthora test (tomato)/curative | |
|---|---|
| Active compound | Infection in % at an active compound concentration of 0.025% |
| (A) | 15 |
| (1) | 1 |
| (5) | 1 |
| (2) | 15 |

EXAMPLE 11

Seed dressing test/bunt of wheat (seed-borne mycosis)

To produce a suitable dry dressing, the active compound was extended with a mixture of equal parts by weight of talc and kieselguhr to give a finely powdered mixture with the desired concentration of the active compound.

Wheat seed was contaminated with 5 g of the chlamydospores of *Tilletia caries* per kg of seed. To apply the dressing, the seed was shaken with the dressing in a closed glass flask. The seed, on moist loam under a cover of a layer of muslin and 2 cm of moderately moist compost soil, was exposed to optimum germination conditions for the spores for 10 days at 10° C. in a refrigerator.

The germination of the spores on the wheat grains, each of which was contaminated with about 100,000 spores, was subsequently determined microscopically. The smaller the number of spores which had germinated, the more effective was the active compound.

The active compounds, the concentrations of the active compounds in the dressing, the amounts of dressing used and the percentage spore germination can be seen from the following table:

Table 4

| Seed dressing test/bunt of wheat | | | |
|---|---|---|---|
| Active compounds | Active compound concentration in the dressing in % by weight | Amount of dressing used in g/kg of seed | Spore germination in % |
| no dressing | — | — | >10 |
| (B) | 10 | 1 | 0.5 |
| (17) | 10 | 1 | 0.5 |

EXAMPLE 12

Phytotoxicity test

Solvent: 4.7 parts by weight of acetone
Emulsifier: 0.3 part by weight of alkylaryl polyglycol ether
Water: 95 parts by weight The amount of active compound required for the desired concentration of the active compound in the spray liquor was mixed with the stated amount of the solvent and the concentrate was diluted with the stated amount of water, which contained the stated amount of emulsifier. Young tomato plants were sprayed with the spray liquor until dripping wet. After drying off, the plants were set up in a greenhouse at a temperature of +20° C. and about 70% relative atmospheric humidity.

The damage to the plants was evaluated repeatedly. The evaluation was made in accordance with a scale of from 1 to 9: thus, 1 denoted no damage whereas 9 denoted that the plants were totally damaged or dead. The period of observation was a rule 4 days.

The active compounds, active compound concentrations and results can be seen from the following table:

Table 5

| | Phytotoxicity Test |
|---|---|
| Active compound | Damage at an active compound concentration of 0.3% |
| (C) | 4 |
| (1) | 3 |
| (18) | 3 |
| (4) | 3 |
| (12) | 3 |
| (6) | 3 |
| (16) | 3 |
| (5) | 3 |
| (7) | 3 |
| (3) | 3 |
| (8) | 3 |

It will be appreciated that the instant specification and examples are set forth by way of illustration and not limitation, and that various modifications and changes may be made without departing from the spirit and scope of the present invention.

What we claim is:

1. A 1-($\omega$-substituted pentyl)-3-(2-cyano-acetyl)-urea of the formula

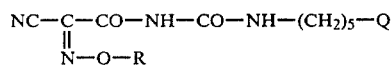

in which
R represents $R^1$, CO—$R^2$, CO—NH—$R^3$ or CO—$OR^4$,
$R^1$ represents unsubstituted alkyl with 1 to 10 carbon atoms; or represents alkyl with 1 to 4 carbon atoms substituted by a member selected from the group consisting of a vinyl group, an alkynyl group with up to 4 carbon atoms, an alkylcarbonyl group with 2 to 5 carbon atoms, an alkoxycarbonyl group with 2 to 5 carbon atoms, an alkenoxycarbonyl or alkynoxycarbonyl group with 4 to 5 carbon atoms, an aminocarbonyl group, an N-alkylaminocarbonyl or N-cycloalkylaminocarbonyl group with up to 7 carbon atoms in either case, or a N-phenylaminocarbonyl group which can optionally have $C_1$–$C_4$ alkyl and/or chlorine as further substituents on said phenyl radical; or represents benzyl; or represents benzyl substituted in the aromatic part by a member selected from the group consisting of a methyl, methoxy, methylenedioxy, nitro, trifluoromethyl, benzoyl, monochlorobenzoyl, dichlorobenzoyl, phenyl or phenoxy group or by 1 to 4 chlorine atoms;
$R^2$ represents a straight-chain or branched, saturated or unsaturated hydrocarbon radical with up to 8 carbon atoms; or a straight-chain or branched, saturated or unsaturated hydrocarbon radical with up to 8 carbon atoms substituted by a member selected from the group consisting of chlorine, bromine or a cyano group,
$R^3$ represents a straight-chain or branched alkyl radical with up to 11 carbon atoms, or represents a straight-chain or branched alkyl radical with up to 11 carbon atoms substituted by a member selected from the group consisting of a cyano group or an alkoxycarbonyl radical with up to 5 carbon atoms, or represents a phenyl radical, or a phenyl radical substituted by member selected from the group consisting of a methyl, nitro or trifluoromethyl group or by chlorine,
$R^4$ represents a saturated or unsaturated aliphatic group with up to 4 carbon atoms,
Q represents CN, CO—$NH_2$, COOH or CO—$OR^5$, and
$R^5$ denotes an alkyl group with 1 to 4 carbon atoms.

2. A compound according to claim 1, in which Q represents CN.

3. A compound according to claim 1, in which R represents $R^1$.

4. A compound according to claim 3, in which
$R^1$ represents alkyl with 1 to 6 carbon atoms; or represents alkyl with 1 or 2 carbon atoms, which is substituted by a member selected from the group consisting of a vinyl group, an alkylcarbonyl group with 2 to 5 carbon atoms, alkoxycarbonyl with 2 to 5 carbon atoms, aminocarbonyl, N-alkylaminocarbonyl or N-cycloalkylaminocarbonyl each with up to 7 carbon atoms, N-phenylaminocarbonyl, and N-phenylaminocarbonyl substituted on the phenyl radical by at least one member selected from the group consisting of $C_1$–$C_4$ alkyl and chlorine; or represents benzyl; or represents benzyl substituted on the aromatic ring by methyl, methoxy, methylenedioxy, nitro, trifluoromethyl, monochloro or dichloro.

5. A compound according to claim 1, wherein said compound is 1-(5-cyanopentyl)-3-(2-cyano-2-methoxyiminoacetyl)-urea of the formula

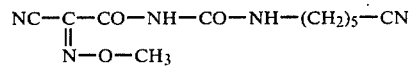

6. A compound according to claim 1, wherein said compound is 1-(5-cyanopentyl)-3-(2-cyano-2-hexyloximino-acetyl)-urea of the formula

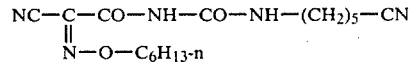

7. A compound according to claim 1, wherein said compound is 1-(5-cyanopentyl)-3-(2-cyano-2-ethoxyimino-acetyl)-urea of the formula

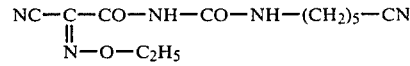

8. A compound according to claim 1, wherein said compound is 1-(5-aminocarbonyl-pentyl)-3-(2-cyano-2-methoxyimino-acetyl)urea of the formula

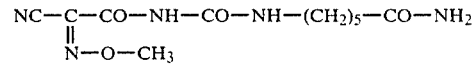

9. A fungicidal composition containing as active ingredient a fungicidally effective amount of a compound according to claim 1 in admixture with a diluent.

10. A method of combating fungi which comprises applying to the fungi, or to a habitat thereof, a fungicidally effective amount of a compound according to claim 1.

11. The method according to claim 10, in which said compound is
1-(5-cyanopentyl)-3-(2-cyano-2-methoxyiminoacetyl)-urea,
1-(5-cyanopentyl)-3-(2-cyano-2-hexyloximinoacetyl)-urea,
1-(5-cyanopentyl)-3-(2-cyano-2-ethoxyiminoacetyl)-urea or
1-(5-aminocarbonyl-pentyl)-3-(2-cyano-2-methoxyimino-acetyl)-urea.

12. A compound of the formula $$NC-\underset{\underset{N-OH}{\parallel}}{C}-CO-NH-CO-N-(CH_2)_5-Q \qquad (IV)$$

in which Q has the meaning stated in claim 1.

* * * * *